United States Patent [19]
Nemeh

[11] Patent Number: 5,135,481
[45] Date of Patent: Aug. 4, 1992

[54] OPHTHAMALIC CANNULA

[76] Inventor: Marwan Nemeh, Bahsah Street, P.O. Box 12139, Damascu, Syria

[21] Appl. No.: 521,349

[22] Filed: May 9, 1990

[51] Int. Cl.⁵ .............................................. A61F 9/00
[52] U.S. Cl. ...................................................... 604/22
[58] Field of Search ............................... 604/22, 29, 43

[56] References Cited

U.S. PATENT DOCUMENTS

| | | | |
|---|---|---|---|
| 3,589,363 | 6/1971 | Banko | 128/276 |
| 3,776,238 | 12/1973 | Peymann et al. | 128/305 |
| 3,815,604 | 6/1974 | O'Malley et al. | 128/305 |
| 3,930,505 | 1/1976 | Wallach | 128/305 |
| 3,990,452 | 11/1976 | Murray et al. | 128/305 |
| 3,996,935 | 12/1976 | Banko | 128/276 |
| 4,014,333 | 3/1977 | McIntyre | 604/43 |
| 4,099,529 | 7/1978 | Peyman | 128/305 |
| 4,167,943 | 9/1979 | Banko | 128/305 |
| 4,188,952 | 2/1980 | Loschilov et al. | 128/305 |
| 4,320,761 | 3/1982 | Haddad | 128/305 |
| 4,428,748 | 1/1984 | Peyman et al. | 604/22 |
| 4,504,264 | 3/1985 | Kelman | 604/22 |
| 4,508,532 | 4/1985 | Drews et al. | 604/22 |
| 4,516,398 | 5/1985 | Wuchinich | 604/22 |
| 4,573,979 | 3/1986 | Blake | 604/240 |
| 4,764,165 | 8/1988 | Reimels et al. | 604/35 |
| 4,790,815 | 12/1988 | Balteau et al. | 604/29 |
| 4,832,683 | 5/1989 | Idemoto et al. | 604/22 |

Primary Examiner—William H. Grieb
Attorney, Agent, or Firm—Fay, Sharpe, Beall, Fagan, Minnich & McKee

[57] ABSTRACT

An ophthamalic instrument suitable for the removal of unwanted tissue and for polishing the posterior capsula of an eye comprises a hollow outer component and a hollow inner component. The hollow outer component has a first and second end, the first end of which is open. The hollow inner component is adapted to be slidingly received within the outer component. The inner component also has a first and second end, the first end being closed and rounded. The inner component has an aperture near the first end through which an associated irrigating medium and dislodged tissue may be aspirated. The first end of the outer component is made of a synthetic resin polymer and is useful for polishing the posterior capsula. The first end of the inner component is made of metal and is selectively extendable beyond the first end of the outer component. When the first end of the inner component is extended beyond the first end of the outer component, it may be used for polishing purposes and for dislodging hardened opacities.

21 Claims, 4 Drawing Sheets

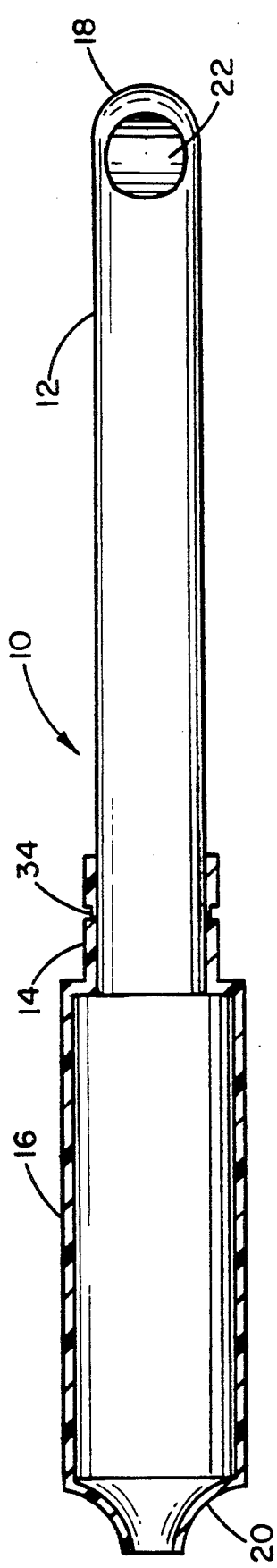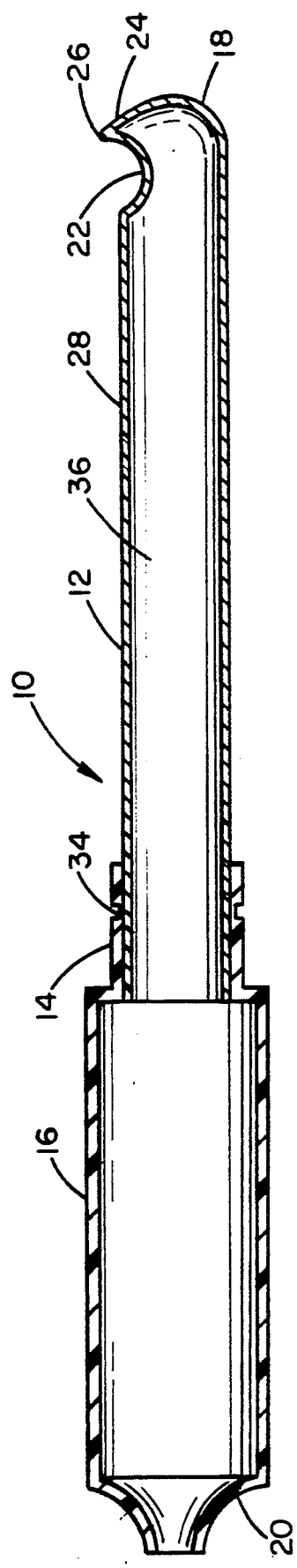

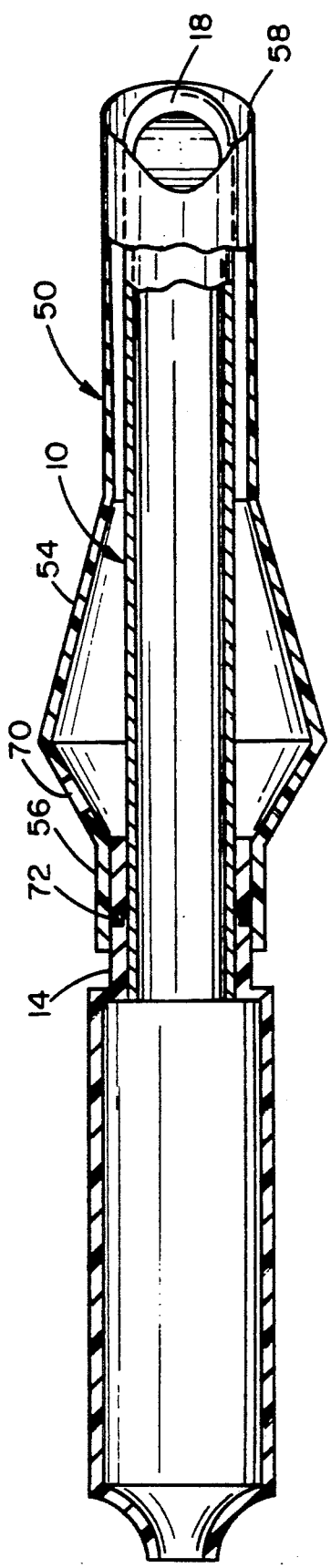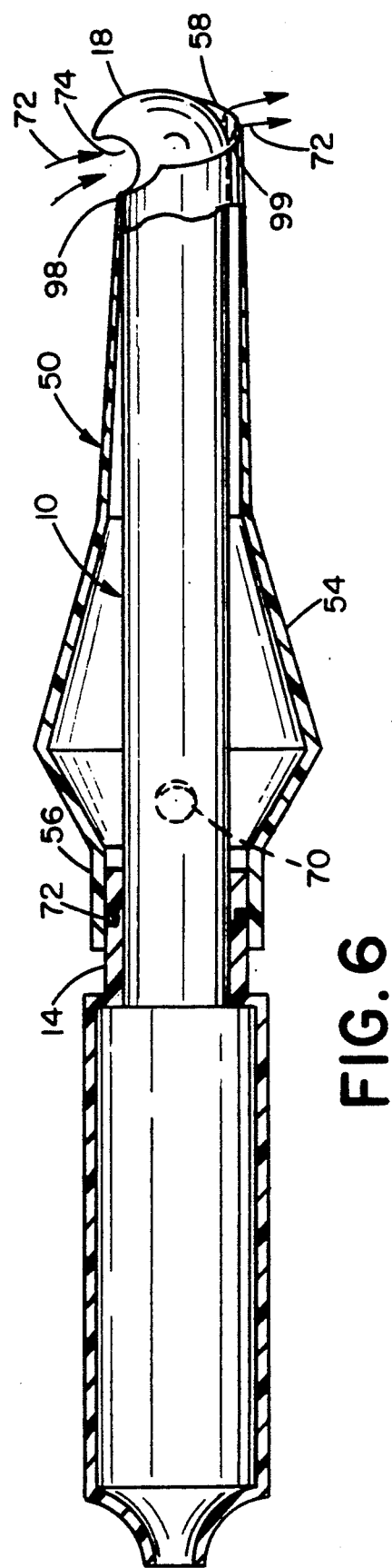

OPHTHAMALIC CANNULA

BACKGROUND OF THE INVENTION

1. Field of the Invention

This invention relates generally to the field of cannulas and more specifically to such cannulas designed for use in cataract removal surgery.

2. Description of the Related Art

Cannulas consisting of two concentric hollow tubes are known in the art. Such cannulas which utilize one of the tubes for aspiration and one of the tube for irrigation are also known. Some such cannulas are equipped with special tips to assist in the polishing operation of the cataract removal surgery. One example of such a cannula is U.S. Pat. No. 3,589,363 to Banko. Additionally, U.S. Pat. No. 4,428,748 to Peyman, et al. discloses a surgical apparatus which provides a cutting tube as well as an ultrasonic motor for driving a needle with ultrasound.

One common problem with such surgical instruments was the difficulty encountered in sterilizing them. In U.S. Pat. No. 4,573,979 to Blake, the outer cannula is disposable while the inner cannula must be sterilized and reused.

Another problem encountered in the art has been the complexity and expense of machines required to control the aspiration and irrigation rates through the cannula. One example of such machine is disclosed in U.S. Pat. No. 4,764,165 to Reimels, et al. One low cost, simple alternative to the more expensive, complicated aspirator/irrigating machines is disclosed in U.S. Pat. No. 4,320,761 to Haddad.

While cataract removal surgery is a common surgical procedure with acceptable success rates, certain problems and deficiencies remain in the surgical apparatuses and cannulas presently used. The need to sterilize the cannulas results in extra cost as well as problems with infection. Because the concentric hollow tubes are so close together, potential for infection remains despite concerted efforts to effectively sterilize the cannula.

Further, the expensive and complicated irrigation/aspiration machines greatly increase the cost of equipment necessary to perform this operation.

Additionally, large amounts of irrigating media, such as saline solution, are often associated with such machines. Some feel this large amount of irrigating media is unnecessary and unhealthy to the patient.

Further, in some patients the cataracts return, a phenomenon known as "after cataract". With some removal mechanisms, the occurrence of after cataract is as high as 20%.

Finally, in some form of cataracts, the tips associated with current devices are unsatisfactory in removing hardened calcifications in the eye. The current invention overcomes each of these deficiencies in some measure.

SUMMARY OF THE INVENTION

In accordance with the present invention, a new and improved ophthamalic instrument suitable for the removal of associated unwanted tissue and for polishing the posterior capsule of an eye is provided.

More particularly, in accordance with the invention, an ophthamalic instrument suitable for the removal of associated unwanted tissue and for polishing the posterior capsule of the eye comprises a hollow outer component and a hollow inner component. The inner component has first and second ends, with the first end of the outer component being open. The inner component is adapted to be slidingly received within the outer component. The inner component also has first and second ends. The inner component has an aperture near the first end. The first end of the inner component is closed is rounded.

In accordance with another aspect of the invention, the inner component further comprises a body portion, the aperture near the first end of the inner component being in the body portion.

In accordance with another aspect of the invention, the rounded first end of the inner component extends slightly outwardly of the aperture as an overhang.

In accordance with another aspect of the invention, the inner component further comprises a body portion, the overhang extending slightly outwardly of the body portion of the inner component.

According to a further aspect of the invention, the outer component is further characterized by the overhang of the first end of the inner component being adapted to selectively slidingly fit into a notch in the first end of the outer component.

According to another aspect of the invention, the first end of the outer component is adapted for polishing the posterior capsula According to a further aspect of the invention, the first end of the outer component is made of a non-pyrogenic synthetic resin polymer.

According to another aspect of the invention, the first end of the inner component is adapted for polishing the posterior capsula by removing hard opacities.

According to a further aspect of the invention, the inner component is made of metal.

According to another aspect of the invention, the aperture in the inner component is triangularly shaped, with the base of the triangle toward the first end of the inner component and the apex of the triangle toward the second end of the inner component.

According to another aspect of the invention, an associated irrigating medium is selectively transferable through the interior of the outer component, the irrigating medium exiting the inner component through the open, first end of the outer component.

According to another aspect of the invention, an associated irrigating medium and associated unwanted tissue are selectably aspiratable through the aperture near the first end of the inner component.

According to another aspect of the invention, the external surface of the inner component is contiguous with the inner surface of the outer component at a point near the aperture in the inner component.

According to a further aspect of the invention, an associated irrigating medium is selectively discharged from the outer component and selectively aspirated through the aperture in the inner component. The contiguousness of the inner surface of the outer component and the outer surface of inner component precludes the irrigating medium from exiting the outer component in the region near the aperture in the inner component.

According to a further aspect of the invention, the inner component is made of a material able to be plastically deformed when stressed by the user's hands.

According to a further aspect of the invention, the thickness of the inner component and the material of which it is made enables the inner component to be bent and plastically deformed by stresses generated by the user's hands.

According to a further aspect of the invention, a method of irrigation and aspiration using a cannula comprises the steps of irrigating the work area by introducing an irrigating medium into the outer component near its second end, the irrigating medium exiting the outer component at points other than those contiguous with the aperture in the inner component, manipulating the cannula to dislodge associated unwanted tissue, and aspirating the associated unwanted tissue and the associated irrigating medium into the aperture and up through the inner component In this method, the cannula comprises a hollow outer component having a first and second end. The first end of the outer component being open. The hollow inner component is adapted to be slidingly received within the outer component. The inner component has an aperture near the first end. An associated irrigating medium and associated unwanted tissue are selectively aspiratable through the aperture in the inner component. The external surface of the inner component is contiguous with the inner surface of the outer component at a point near the aperture in the inner component. The contiguousness of the inner surface of the outer component and the outer surface of the inner component precludes the irrigating medium from exiting the outer component in the region near the aperture in the inner component.

According to a further aspect of the invention, a method of removing opacities from the posterior capsula using a cannula comprises irrigating the work area, mobilizing the associated unwanted opacities by manually polishing while irrigating with no aspiration, and aspirating the opacities along with the irrigating medium. The cannula to be used with this method comprises an outer component and an inner component. The inner component is slidingly received within the outer component and has an aperture on one side. The cannula is operatively adapted to selectively irrigate through the outer component and selectively aspirate through the inner component. An associated irrigating medium is selectively dischargeable from the outer component. The majority of the irrigating medium exits the outer component at a point farthest from the aperture in the inner component.

According to a further aspect of the invention, the first end of the inner component is closed and rounded in a nearly spherical shape. One edge of the aperture is contiguous with the equator of the spherically-shaped first end.

According to another aspect of the invention, the inner component comprises a syringe portion, an interface portion, and a body portion. A sealing means for sealing the sliding interface is located between the second end of the outer component and the interface portion of the inner component.

According to a further aspect of the invention, the sealing means for sealing is a ring made of a non-pyrogenic elastomer.

According to another aspect of the invention, a vacuum means to draw a vacuum is connected to the second end of the inner component so that a vacuum is selectively creatable at the first end of the inner component. The vacuum created is able to aspirate an associated irrigating fluid and associated unwanted tissue through the aperture, through the interior of the body portion, and into the syringe portion of the inner component.

According to another aspect of the invention, a pressurizing means is provided to deliver an associated irrigating medium under pressure through an inlet aperture in the outer component. Additionally, a controlling means for controlling is provided to control the flow rate of the irrigating medium flowing into the inlet aperture in the outer component.

According to a further aspect of the invention, the vacuum means is a syringe.

According to a further aspect of the invention, the pressurizing means to deliver the associated irrigating medium is a reservoir of the associated irrigating medium elevated above the inlet aperture.

According to another aspect of the invention, the control means to control the flow rate of the associated irrigating medium is a stopcock.

According to another aspect of the invention, the outer component further comprises a body portion, a cone portion, and an interface portion. The cone portion is sized to fit comfortably in a person's hand. The cone portion has an inlet aperture for the introduction of an associated irrigating fluid. The interface portion of the outer component is operatively associated with the interface portion of the inner component. The interface portion of the inner component is selectively slidable relative to the interface portion of the outer component, such sliding effective to selectively extend the first end of the inner component outwardly of the first end of the outer component.

According to a further aspect of the invention, the inner component is made of metal and the outer component is made of a non-pyrogenic synthetic resin polymer. The polymer and the metal are such that the instrument is inexpensive and completely disposable after one use.

According to a further aspect of the invention, a method of irrigation and aspiration for use in ophthamalic surgeries is disclosed. The method comprises the steps of hanging a reservoir of the associated irrigating medium at an elevation greater than the point of discharge, controlling the flow rate of the irrigating medium via a controlling means to control the flow rate, and aspirating the irrigating medium along with any associated unwanted tissue by drawing a vacuum, the vacuum created by withdrawing the plunger of a syringe.

According to a further aspect of the invention, a method of polishing the posterior capsula of an eye comprises the steps of inserting a cannula into the eye, polishing the posterior capsula by suctioning associated unwanted tissue and by manually causing a first tip of the cannula to touch the posterior capsula, and polishing the posterior capsula by extending a second tip from the cannula and manually manipulating the second tip to remove associated unwanted hardened opacities.

According to a further aspect of the invention, a method of polishing the posterior capsula of an eye is disclosed. This method comprises the steps of inserting a cannula into the eye, irrigating the eye with an associated irrigating fluid, polishing the posterior capsula by manually manipulating a first tip of the cannula, extending a second tip of the cannula beyond the first tip, polishing the posterior capsula by manually manipulating a second tip of the cannula to remove associated unwanted hardened opacities, and suctioning away undesirable tissue floating in the irrigating fluid.

According to a further aspect of the invention, a method of a cataract surgery is disclosed which comprises the steps of incising the eye, cauterizing the blood vessels, puncturing the anterior capsula with a syringe, injecting fluid to form the anterior chamber, puncturing the anterior chamber in a circular fashion, extracting the nucleus of the cataract, suturing the incision leaving two openings, the openings being separated by a distance of about 1.5 mm, inserting a cannula into one of the openings, aspirating the remnants of the cortex, polishing the posterior capsula with a first tip of the cannula, the polishing performed with irrigation but with no aspiration, aspirating loose tissue, extending a second tip in the cannula beyond the first tip, polishing the posterior capsula by manually manipulating the second tip to dislodge associated unwanted hardened opacities, the polishing performed with irrigation but with no aspiration, aspirating all remnants of the opacities and other undesirable tissues, and suturing the two openings.

According to a further aspect of the invention, a cannula for ophthamalic procedures comprises a first tip adapted for polishing the posterior capsula and a second tip adapted for polishing the posterior capsula.

According to another aspect of the invention, each of the tips of the cannula engages and dislodges associated unwanted tissue on the posterior capsula.

According to another aspect of the invention, means for extending one tip beyond the other tip is provided so that only one tip is operatively engaging the posterior capsula at a time.

According to another aspect of the invention, the first tip of the capsula is made of a non-pyrogenic synthetic resin polymer.

According to a further aspect of the invention, the second tip of the capsula is made of metal.

One advantage of the present invention is to reduce the amount of associated irrigating media which is commonly used in a cataract removal operation. The large amounts of irrigation associated with some such operations can be injurious to the endothelium.

Another advantage of the present invention is the improved control available to the surgeon in the amount and rate of irrigation and aspiration.

Another advantage of the present invention is its disposable nature. The low cost and simple construction of the present invention allows it to be completely disposable after one use. Other such instruments require partial or total sterilization and repeated use, as they are expensive and complicated. Sterilization of such instruments is difficult and a risk of infection is present.

Another advantage of the present invention is its low cost due to its simple construction.

Another advantage of the present invention is that it offers the surgeon two different polishing tips. The first tip is made of a synthetic resin polymer and is suitable for dislodging and aspirating most remnants In the case of hardened opacities and calcifications, a second smooth metal tip may be extended beyond the first tip and may be used by the surgeon to dislodge and mobilize the hardened opacities.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein:

FIG. 1 is a cross-sectional view of the inner component;

FIG. 2 is a partially broken-away, cross-sectional view of the inner component rotated approximately 90° from the view shown in FIG, 1;

FIG. 5 is a partially broken-away cross-sectional view of the ophthamalic instrument with the inner component inserted within the outer component, with the first end of the inner component retracted within the outer component;

FIG. 6 is a partially broken-away cross-sectional view of the ophthamalic instrument rotated 90° from the view shown in FIG. 5, with the first end of the inner component extended outwardly of the first end of the outer component; and, FIG. 7 is a schematic cross-sectional view of the ophthamalic instrument including a pressurizing means and a vacuum means.

DESCRIPTION OF THE PREFERRED EMBODIMENT

Figure 3:
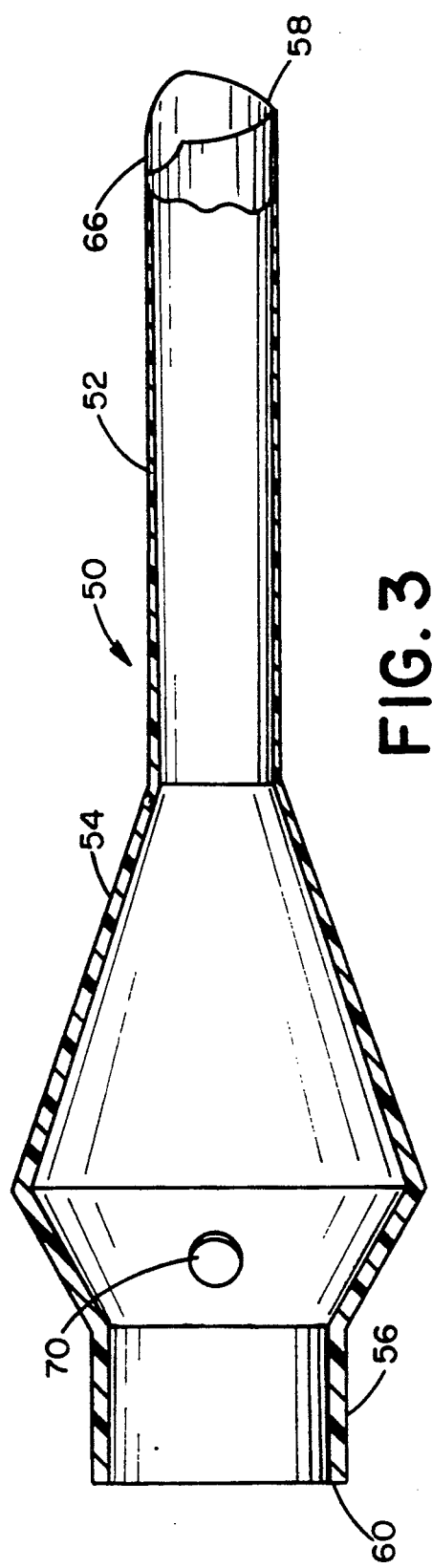
FIG. 3 is a partially broken-away cross-sectional view of the outer component.

Referring now to the drawings wherein the showings are for purposes of illustrating a preferred embodiment of the invention only and not for purposes of limiting the same, FIGS. 1 and 2 show a cross-sectional view of the inner component 10. The inner component is comprised of a body portion 12, an interface portion 14, and a syringe portion 16. The inner component has a first end 18 and a second end 20. An aperture 22 is located near the first end 18 of the inner component.

The first end 18 of the inner component 10 is closed and is formed into a rounded shape. In the preferred embodiment, the first end is nearly spherically-shaped. The surface between the aperture 22 and the first end 18 of the inner component 10 is formed into an overhang 24. The outward-most extent 26 of the overhang 24 extends outwardly of the walls 28 of the body portion 12 of the inner component 10. "Outer" or "outwardly" means away from the longitudinal axis of the instrument, while "inner" means towards the longitudinal axis. The outer surface of the first end 18 of the inner component 10, the overhang 24, is formed into a smooth surface 30. This surface is adapted for dislodging and polishing of hardened opacities such as calcifications.

Into the outer surface of the interface portion 14 of the inner component 10 is formed a groove 34. The groove 34 extends circumferentially around the interface portion 14 of the inner component 10 and is adapted to receive a ring of non-pyrogenic elastomeric material. The operation of this ring will be discussed later in this description.

The syringe portion 16 of the inner component 10 is adapted to receive an associated irrigating medium and pieces of unwanted tissue which are aspirated through the aperture 22. When a source of vacuum is applied to the second end 20 of the inner component 10, a negative pressure, or vacuum, is created at the aperture 22. When the aperture 22 is immersed in an irrigating medium, the vacuum at the aperture 22 causes the irrigating medium, along with unwanted tissue and hardened opacities which have been dislodged and suspended in the irrigating medium, to enter the interior 36 of the inner component 10 and progress towards the syringe portion 16.

Figure 4:
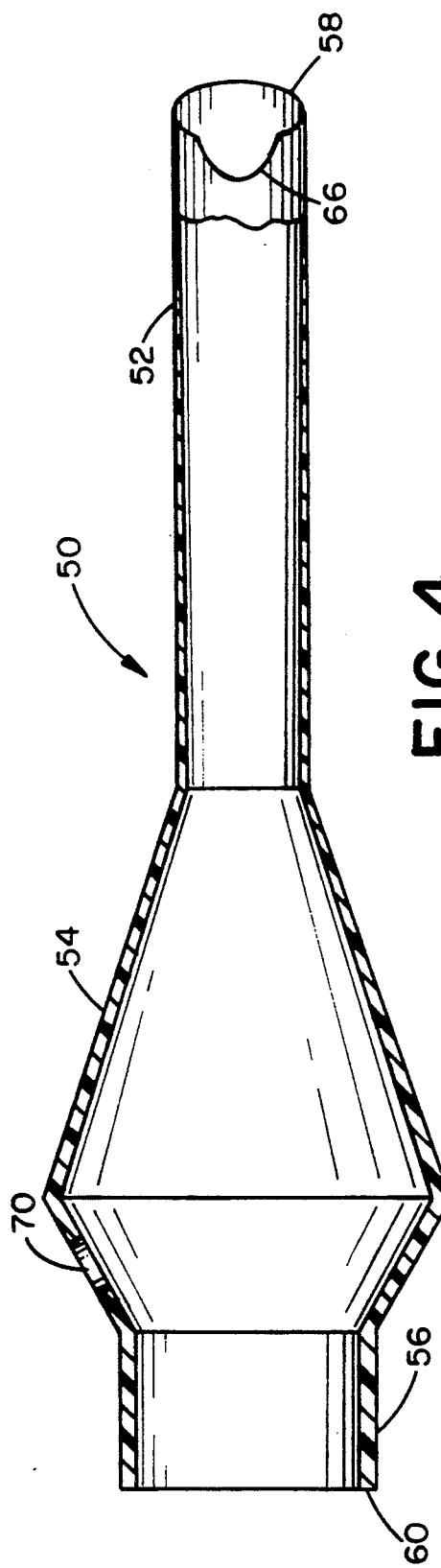
FIG. 4 is a partially broken-away, cross-sectional view of the outer component rotated approximately 90° from the view shown in FIG. 3.

With reference now to FIGS. 3 and 4, the outer component 50 comprises a body portion 52, a cone portion 54, and an interface portion 56. The outer component 50 has a first end 58 and a second end 60.

The outer component is manufactured of a non-pyrogenic synthetic resin polymer. In the preferred embodiment, this polymer is polytetrafluroethylene (PTFE).

The first end 58 of the outer component 50 is open. Additionally, the first end 58 is characterized by a notch 66 which is formed into the first end 58 of the outer component 50.

An inlet aperture 70 is formed through the wall of the cone portion 54 of the outer component 50. The inlet aperture 70 functions as a conduit for an associated irrigating medium such as saline solution.

With reference now to FIGS. 5 and 6, there is disclosed the configuration of the inner component and outer component when the instrument is in normal use. Namely, the inner component 10 is slidingly received within the outer component 50. The interface portion 14 of the inner component 10 and the interface portion 56 of the outer component 50 are operatively adapted to slide relative to each other. This sliding is facilitated in part by a ring 72 which is received in a groove 34 which was discussed earlier. The ring 72 is made of a non-pyrogenic elastomer and serves to seal associated irrigating medium which enters the outer cone portion 54 through the inlet aperture 70 and prevents such irrigating media from exiting the outer component 50 in any place except the first end 58 of the outer component.

In FIG. 6, the inner component 10 has been pushed outwardly through the outer component 50 so that the first end 18 of the inner component 10 extends outwardly of the first end 58 of the outer component 50. In contrast, in FIG. 5, the inner component 10 has been withdrawn within the outer component 50 so that the first end 18 of the inner component 10 is contained within the first end 58 of the outer component 50.

The sliding of interface portion 14 of the inner component 10 relative to the interface portion 56 of the outer component 50 allows the user of this ophthamalic instrument to choose either the first end 18 of the inner component 10 or the first end 58 of the outer component 50 for polishing purposes.

With continuing reference to FIG. 6, the associated irrigating medium 72 is introduced to the cannula through inlet aperture 70 of the outer component 50. The irrigating medium continues out the first end 58 of the outer component 50 by the force of gravity. It is advantageous that the irrigating medium 72 enter the work area and suspend dislodged tissue before being aspirated into the aperture 22 of the inner component 10. To accomplish this objective, the outer surface of the inner component 10 is bent to be contiguous to the inner surface of the outer component 50 at a point 98 near the apex of the aperture 22. The contiguousness of the inner component 10 and the outer component 50 precludes any irrigating medium 72 from exiting the outer component 50 at this point. Therefore, the majority of the irrigating medium 72 exits the outer component 50 at a point 99 which is 180° from the aperture 22. This forces the irrigating medium to bathe the work area and suspend any tissue which has been dislodged by the polishing tips 18, 58. Then the irrigating medium, including suspended tissue, is drawn to the area 74 adjacent the aperture 22 in the inner component 10 and aspirated into the syringe portion 16.

The inner component 10 is made of a material and of a wall thickness that enables the inner component 10 to be bent and plastically deformed by stresses generated by the eye surgeon's hands. For example, the currently preferred embodiment of the inner component is made of metal of a 20 G(gauge) thickness.

Figure 7:
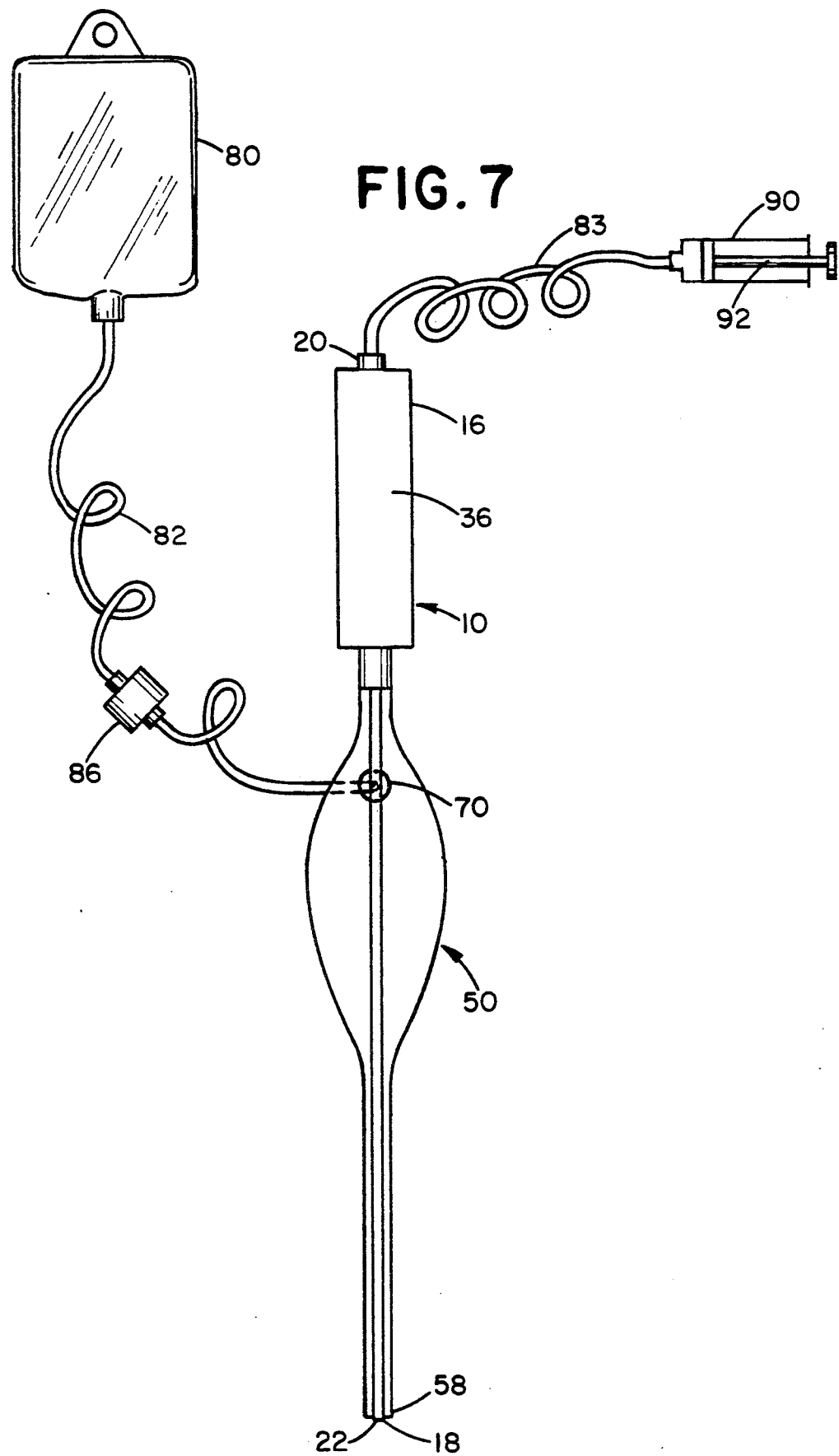

With reference now to FIG. 7, there is disclosed a simple and inexpensive system to deliver an associated irrigating medium, such as saline solution, under pressure to the inlet aperture 70 of the outer component 50. Additionally, vacuum means is disclosed to provide a vacuum at the aperture 22 of the inner component 10.

With particular reference now to FIG. 7, there is disclosed a reservoir 80 of an associated irrigating medium. The reservoir 80 is connected to the inlet aperture 70 of the cone portion 54 of the outer component 50 via tubing 82. Located in the tubing 82 between the reservoir 80 and the inlet aperture 70 is a manual valve or stopcock 86. This manual valve or stopcock can be easily manipulated by the surgeon, without the help of an assistant, in the midst of the operation to provide the proper flow rate of the associated irrigating medium.

Additionally, at the second end 20 of the inner component 10 is shown additional tubing 83 leading to a syringe 90 shown in cross-section. By withdrawing the plunger 92 from the syringe 90, a negative pressure or vacuum is created in the syringe, in the tubing 83 and in the syringe portion 16 of the inner component 10. Eventually, this negative pressure is experienced at the aperture 22 of the inner component 10. This vacuum causes an aspiration process in which the associated irrigating medium is drawn from the eye into the interior 36 of the inner component 10.

With reference now to FIGS. 5-7, in a typical operation, the surgeon will remove the cataract, leaving remnants needing to be aspirated With the current invention, the surgeon can first mobilize these remnants via a gentle polishing action with the first end 58 of the outer component 50. The first end 58 of the outer component 50 is made of a non-pyrogenic synthetic resin polymer such as polytetrafluroethylene (PTFE). This soft material is effective in dislodging and aspirating most remnants. In this mode, the first end 18 of the inner component 10 is withdrawn within the notch 66 of the first end 58 of the outer component 50, as shown in FIG. 5. Preferably, this gentle polishing action is performed with irrigation alone and without aspiration. When aspirating, because of the suction formed by the vacuum at the aperture 22, it is possible to damage the posterior capsula. By polishing with irrigation alone, the remnants may be gently dislodged by the first end 58 of the outer component and suspended in the associated irrigating medium. The remnants, along with the irrigating medium, may be safely aspirated through the aperture 22 when fully dislodged.

Should the surgeon encounter hardened opacities, such as areas of calcification, the first end 58 of the outer component 50 may prove to be ineffective in dislodging and aspirating same. In such a case, the surgeon can manipulate the instrument such that the interface portion 14 of the inner component 10 is pushed downwardly farther into the outer component 50. This is accomplished by relative sliding by the interface portions 14, 56 of the inner component 10 and the outer component 50. Such sliding extends the first end 18 of the inner component 10 outwardly of the first end 58 of the outer component 50. This exposes the smooth, nearly spherical first end 18 of the inner component 10 to the posterior capsula and the hardened opacities. The first end 18 of the inner component 10 is especially useful in dislodging hardened opacities and calcifications such as are encountered in the eyes of children. Although the smooth steel first end 18 is effective in removing such hardened opacities, it does not damage the posterior capsula. This polishing is also performed with irrigation alone and not with aspiration. After the hardened opacities are dislodged and suspended in the irrigating medium, they may be aspirated through aperture 22 as before.

The gentle polishing action of the second end 58 of the outer component 50 and the first end 18 of the inner component 10, along with careful control of the irrigation and aspiration process have resulted in a low incidence of "after cataract". The inventor believes the low occurrence of after cataract is due in part to the thoroughness by which the cataract can be removed, the gentleness of the process with the current invention, the limited amount of irrigating fluid necessary to perform the operation, and the sterility of the invention due to its disposable nature.

The low cost and simple construction of this invention allows the invention to be completely disposable, eliminating any need for problematic sterilization. The aspiration rate can be effectively and carefully controlled with the syringe 90. A significant advantage of this invention is that the rate of aspiration and irrigation may be effectively controlled in the amount of irrigating and aspirating fluids significantly reduced. The surgeon is free to manipulate either the first end 18 of the inner component 10 or the first end 58 of the outer component 50 without any irrigation or aspiration at all. This eliminates the possibility of suctioning the surface of the posterior capsula into the aperture 22 while polishing. Additionally, some surgeons feel a lower rate of irrigation is safer and healthier for the patient.

The invention has been described with reference to a preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. An ophthamalic instrument suitable for removal of unwanted tissue and for polishing the posterior capsula, the instrument comprising:
   a hollow outer component having first and second ends, the first end of the outer component being opened;
   a hollow inner component slidingly received within the outer component, the inner component having first and second ends, the inner component having an aperture near the first end, the first end being close and rounded, the rounded first end of the inner component extending slightly outwardly of the aperture in the inner component as an overhang; and,
   a notch, the notch being located in the first end of the outer component, the overhang of the first end of the inner component selectively slidingly fitting into the notch.

2. An ophthamalic instrument suitable for removal of unwanted tissue and for polishing the posterior capsula, the instrument comprising:
   a hollow outer component having first and second ends, the first end of the outer component being open; and,
   a hollow inner component slidingly received within the outer component, the inner component having first and second ends, the inner component having an aperture near the first end, the first end being closed and rounded, the first end of the outer component being made of a non-pyrogenic synthetic resin polymer.

3. An ophthamalic instrument as in claim 7 wherein the outer component is made of a non-pyrogenic synthetic resin polymer.

4. An ophthamalic instrument suitable for removal of unwanted tissue and for polishing the posterior capsula, the instrument comprising:
   a hollow outer component having first and second ends, the first end of the outer component being open; and,
   a hollow inner component slidingly received within the outer component, the inner component having first and second ends, the inner component having an aperture near the first end, the first end being closed and rounded, the aperture in the inner component being triangularly shaped, the base of the triangle being toward the first end of the inner component and the apex of the triangle being toward the second end of the inner component.

5. An ophthamalic instrument suitable for removal of unwanted tissue and for polishing the posterior capsula, the instrument comprising:
   a hollow outer component having first and second ends, the first end of the outer component being open; and,
   a hollow inner component slidingly received within the outer component, the inner component having first and second ends, the inner component having an aperture near the first end, the first end being closed and rounded, an associated irrigating medium and unwanted tissue being selectably aspiratable through the aperture near the first end of the inner component, the external surface of the inner component being contiguous with the inner surface of the outer component at a point near the aperture in the inner component, an associated irrigating medium being selectively discharged from the outer component and selectively aspirated through the aperture in the inner component, the contiguousness of the inner surface of the outer component and the outer surface of the inner component precluding the irrigating medium from exiting the outer component in the region near the aperture in the inner component.

6. An ophthamalic instrument as in claim 5 wherein the inner component is made of a material able to be plastically deformed when stressed by the user's hands.

7. An ophthamalic instrument as in claim 5 wherein the thickness of the inner component and the material of which it is made enables the inner component to be bent and plastically deformed by stresses generated by the user's hands.

8. A method of irrigation and aspiration using a cannula, the cannula comprising:
   a hollow outer component having first and second ends, the first end of the outer component being open; and,
   a hollow inner component adapted to be slidingly received within the outer component, the inner component having an aperture near the first end, an associated irrigating medium and associated unwanted tissue selectively aspiratable through the aperture, the external surface of the inner component contiguous with the inner surface of the outer component at a point near the aperture in the inner component, the contiguous of the inner surface of the outer surface of the inner component precluding the irrigating medium from exiting the outer component in the region near the aperture in the inner component;

the method comprising the steps of:

irrigating the work area by introducing an irrigating medium into the outer component near its second end, the irrigating medium exiting the outer component at points other than those contiguous with the aperture in the inner component;

manipulating the cannula to dislodge undesirable tissue; and, aspirating the tissue and the associated irrigating medium into the aperture and up through the inner component.

9. A method of removing opacities from the posterior capsula using a cannula, the cannula comprising an outer component and an inner component, the inner component slidingly received within the outer component and having an aperture on one side, the cannula operatively adapted to selectively irrigate through the outer component and selectively aspirate through the inner component, an associated irrigating medium selectively dischargeable from the outer component, the majority of the irrigating medium exiting the outer component at the point farthest from the aperture in the inner component, the method comprising the steps of:

irrigating the work area;

mobilizing the associated opacities and other associated tissue by manually polishing while irrigating with no aspiration; and, aspirating the associated opacities and other associated tissue along with the irrigating medium.

10. An ophthamalic instrument suitable for removal of unwanted tissue and for polishing the posterior capsula, the instrument comprising:

a hollow outer component having first and second ends, the first end of the outer component being open; and, a hollow inner component slidingly received within the outer component, the inner component having first and second ends, the inner component having an aperture near the first end, the first end being closed and rounded, the inner component comprising a syringe portion, an interface portion, and a body portion, and further comprising:

sealing means for sealing the sliding interface between the second end of the outer component and the interface portion of the inner component.

11. An ophthamalic instrument as in claim 10 wherein the sealing means is a ring made of a non-pyrogenic elastomer.

12. An ophthamalic instrument as in claim 10 wherein the outer component further comprises:

a body portion;

a cone portion, the cone portion being sized to fit comfortably in a person's hand, the cone having an inlet aperture for the introduction of an associated irrigating fluid; and, an interface portion, the interface portion of the outer component operatively associated with the interface portion of the inner component so that the interface portion of the inner component is selectively slidable relative to the interface portion of the outer component, such sliding effective to selectively extend the first end of the inner component outwardly of the first end of the outer component.

13. An ophthamalic instrument suitable for removal of unwanted tissue and for polishing the posterior capsula, the instrument comprising:

a hollow outer component having first and second ends, the first end of the outer component being open;

a hollow inner component slidingly received within the outer component, the inner component having first and second ends, the inner component having an aperture near the first end, the first end being closed and rounded; and, vacuum means to draw a vacuum, the vacuum means connected to the second end of the inner component, so that a vacuum is selectively creatable at the first end of the inner component, the vacuum able to aspirate an associated irrigating fluid and associated unwanted tissue through the aperture, through the interior of the body portion, and into the syringe portion.

14. An ophthamalic instrument as in claim 13 wherein the vacuum means is a syringe.

15. An ophthamalic instrument suitable for removal of unwanted tissue and for polishing the posterior capsula, the instrument comprising:

a hollow outer component having first and second ends, the first end of the outer component being open;

a hollow inner component slidingly received within the outer component, the inner component having first and second ends, the inner component having an aperture near the first end, the first end being closed and rounded;

an inlet aperture in the outer component, the inlet aperture being located near the second end of the outer component and selectively receiving an associated irrigating medium;

pressurizing means to deliver an irrigating medium under pressure through the inlet aperture in the outer component; and, controlling means for controlling the flow rate of the associated irrigating medium flowing into the inlet aperture in the outer component.

16. An ophthamalic instrument as in claim 15 wherein the pressurizing means to deliver the irrigating medium is a reservoir of the associated irrigating medium elevated above the inlet aperture.

17. An ophthamalic instrument as in claim 16 wherein the control means for controlling the flow rate of the irrigating medium is a stopcock.

18. An ophthamalic instrument suitable for removal of unwanted tissue and for polishing the posterior capsula, the instrument comprising:

a hollow outer component having first and second ends, the first end of the outer component being open; and, a hollow inner component slidingly received within the outer component, the inner component having first and second ends, the inner component having an aperture near the first end, the first end being closed and rounded, the inner component is made of metal and the outer component is made of a non-pyrogenic synthetic resin polymer, the resin and metal such that the instrument is inexpensive so as to be completely disposable after one use.

19. A method of polishing the posterior capsula of an eye, the method comprising the steps of:
   inserting a cannula into the eye;
   polishing the posterior capsula by suctioning any associated unwanted tissue and by manually causing a first tip of the cannula to touch the posterior capsula; and,
   polishing the posterior capsula by extending a second tip from the cannula and manually manipulating the second tip to remove associated hardened opacities.

20. A method of polishing the posterior capsula of an eye, the method comprising the steps of:
   inserting a cannula into the eye;
   irrigating the eye with an associated irrigating fluid;
   polishing the posterior capsula by manually manipulating a first tip of the cannula;
   extending a second tip of the cannula beyond the first tip;
   polishing the posterior capsula by manually manipulating a second tip of the cannula to remove hardened opacities; and,
   suctioning away associated unwanted tissue floating in the associated irrigating fluid.

21. An ophthamalic instrument suitable for removal of associated unwanted tissue and for polishing the posterior capsula, the instrument comprising:
   a hollow outer component having first and second ends, the first end of the outer component being open, the first end of the outer component being made of a non-pyrogenic synthetic resin polymer and being adapted for polishing the posterior capsula, the first end of the outer component having a notch therein, the outer component further comprising a body portion, a cone portion, and an interface portion, the cone portion being sized to fit comfortably in a person's hand and having an inlet aperture for the introduction of an associated irrigating fluid, the outer component being made of a non-pyrogenic synthetic resin polymer;
   a hollow inner component adapted to be slidingly received within the outer component, the inner component comprising a syringe portion, an interface portion, a body portion, a first end, and a second end, the first end being closed and rounded, the inner component having an aperture near the first end, the aperture being triangularly shaped, with the base of the triangle toward the first end of the inner component and the apex of the triangle toward the second end of the inner component, the rounded first end of the inner component extending slightly outwardly of the aperture as an overhang, the overhang being adapted to selectively slidingly fit into the notch in the first end of the outer component, the interface portion of the outer component operatively associated with the interface portion of the inner component so that the interface surface of the inner component is selectively slidable relative to the interface surface of the outer component, such sliding effective to selectively extend the rounded first end of the inner component outwardly of the first end of the outer component;
   a sealing means for sealing the sliding interface between the second end of the outer component and the interface portion of the inner component, the sealing means being a ring made of a non-pyrogenic elastomer;
   a vacuum means to draw a vacuum, the vacuum means connected to the second end of the inner component so that a vacuum is selectively creatable at the first end of the inner component, the vacuum able to aspirate fluid and tissue through the aperture, through the interior of the body portion of the inner component, and into the syringe portion of the inner component;
   a pressurizing means to deliver an associated irrigating medium under pressure through an inlet aperture in the outer component; and,
   a controlling means for controlling the flow rate of the associated irrigating medium flowing into the inlet aperture in the outer component.

* * * * *